(12) United States Patent
Chen et al.

(10) Patent No.: US 8,686,191 B2
(45) Date of Patent: Apr. 1, 2014

(54) ENVIRONMENTALLY-FRIENDLY NEW OXIDATION PROCESS FOR CONVERTING ARYL-1,2-DIOL TO KETONE

(75) Inventors: Ting Chen, Shenzhen (CN); Yu Wang, Shenzhen (CN)

(73) Assignee: Shenzhen Liv-Chemth Co., Lto, Shenzhen (CN)

( * ) Notice: Subject to any disclaimer, the term of this patent is extended or adjusted under 35 U.S.C. 154(b) by 0 days.

(21) Appl. No.: 13/811,903

(22) PCT Filed: Dec. 29, 2011

(86) PCT No.: PCT/CN2011/002210
§ 371 (c)(1),
(2), (4) Date: Jan. 23, 2013

(87) PCT Pub. No.: WO2012/100403
PCT Pub. Date: Aug. 2, 2012

(65) Prior Publication Data
US 2013/0296611 A1 Nov. 7, 2013

(30) Foreign Application Priority Data
Jan. 28, 2011 (CN) .......................... 2011 1 0032160

(51) Int. Cl.
*C07C 45/29* (2006.01)
*C07C 45/30* (2006.01)

(52) U.S. Cl.
USPC .......................................... 568/311; 568/323

(58) Field of Classification Search
USPC .................................................... 568/311, 323
See application file for complete search history.

(56) References Cited

U.S. PATENT DOCUMENTS

| 2005/0203315 A1* | 9/2005 | Grutzmacher et al. | ....... 568/360 |
| 2009/0018354 A1* | 1/2009 | End et al. | ..................... 549/519 |

OTHER PUBLICATIONS

Sharma et al. Kinetics and mechanism of the oxidation of diols by bromine in acid solution. Proc. Indian Acad. Sci. (Chem. Sci.), vol. 110, No. 1, Feb. 1998, pp. 65-73.*

* cited by examiner

*Primary Examiner* — Sikarl Witherspoon
(74) *Attorney, Agent, or Firm* — CBM Patenting Consulting, LLC

(57) ABSTRACT

The present invention relates to the technical field of radiation curing photopolymerization initiator, and particularly to an environmentally-friendly new oxidation process for converting several specific aryl-1,2-diol compounds to corresponding arylhydroxyketones.

11 Claims, No Drawings

ENVIRONMENTALLY-FRIENDLY NEW OXIDATION PROCESS FOR CONVERTING ARYL-1,2-DIOL TO KETONE

FIELD OF THE INVENTION

The present invention relates to the technical field of radiation curing photopolymerization initiators, and particularly to an environmentally-friendly new oxidation process for converting several specific aryl-1,2-diol compounds to their corresponding aryl hydroxyketones.

BRIEF DESCRIPTION OF BACKGROUND ART

In UV-curing industry it is well known that the following three aryl hydroxyketone compounds 1-3 are very important photo-initiators for UV-radiation photopolymerizations of olefinically unsaturated systems.

Compound 1: 2-hydroxy-2-methyl-1-phenyl-1-propanone, its CAS number is 7473-98-5.

Compound 2: (1-hydroxycyclohexyl)phenyl-methanone, its CAS number is 947-19-3.

Compound 3: 2-hydroxy-1-(4-methoxyphenyl)-2-methyl-1-propanone, its CAS number is 15482-17-4.

Traditional production processes for compounds 1-3 involve so-called Friedel-Crafts reactions, which typically employes excess anhydrous Lewis acid $AlCl_3$ and highly toxic $Cl_2$ gas as key raw materials, thereby incuring the generations of massive amounts of solid wastes and acidic and basic by-products. Not surprisingly, such technologies are now experiencing increasingly stringent environmental protection pressure. Patent applications US2009/0018354A1 and US2005/0203315A1 had each disclosed new preparation methods for compounds 1-3 through oxidizing their corresponding aryl 1,2-diol precursors. Unfortunately, the oxidants they employed are such heavy-metals as Pd and Cu and their relevant complexes, which are not only prohibitively costly, but also difficult to access and labile for incurring heavy-metal-related environmental pollutions. Thus, there exists a strong need for developing truly "green" and economically sounding production methods for compounds 1-3.

The present invention has now for the first time disclosed that, surprisingly, compounds 1-3 can be simply prepared by oxidizing their corresponding aryl 1,2-diol precursors with $Br_2$ as the oxidant; or alternatively, with $Br_2$ as the oxidation catalyst in conjunction with $H_2O_2$ (hydrogen peroxide) as the terminal oxidant. The significant advantages of this invention over the previously known methods are high product yields, economical competitiveness, and environmental friendliness.

SUMMARY OF THE INVENTION

The present invention aims at introducing a new method for producing compounds 1-3 by oxidizing their corresponding aryl 1,2-diol precursors with $Br_2$ as the oxidant, or alternatively, with $Br_2$ as the oxidation catalyst in conjunction with $H_2O_2$ as the terminal oxidant. The said aryl 1,2-diol precursors are the following compounds:

Compound 4: 2-methyl-1-phenyl-1,2-propanediol, its CAS number is 20907-13-5.

Compound 5: α-(1-hydroxycyclohexyl)-benzene-methanol, its CAS number is 1135-72-4.

Compound 6: 1-(4-methoxyphenyl)-2-methyl-1,2-propanediol, its CAS number is 261930-06-7.

The disclosed new oxidation technology follows one of the two illustrated general chemical reaction schemes A or B (see below).

Reaction scheme A involves two steps: in step one the said diol compounds 4-6 was each oxidized by $Br_2$ to produce their corresponding ketone products 1-3 and by-product HBr. In this step reaction temperature is preferably room temperature, and solvents are preferably selected from chlorinated hydrocarbons such as $CH_2Cl_2$. The optimal amounts of $Br_2$ employed are one-to-three equivalents relative to the diol substrate. The key feature of this step is the use of $Br_2$ as the oxidant. In step two, the by-product HBr generated from the above step one was contacted with $H_2O_2$ to enable the recycling of $Br_2$. The reaction temperature is preferably room temperature, and the ratio of $HBr/H_2O_2$ is preferably ranging from 2/1 to 1/1, and the concentration of aqueous $H_2O_2$ solution is preferably ranging from 10-50% wt.

Reaction scheme B involves only one step, i.e., it is a "one-pot" process, in which $Br_2$ was used as the catalyst for oxidizing diol substrates 4-6 into their corresponding products 1-3 with $H_2O_2$ as the terminal oxidant. The reaction temperature is preferably room temperature, and solvents are preferably selected from chlorinated hydrocarbons such as $CH_2Cl_2$. The optimal amounts of $Br_2$ catalyst employed are 0.05-0.70 equivalents relative to the diol substrate, and the optimal amounts of $H_2O_2$ used are 1-20 equivalents. An important variant for executing this "one-pot" process is the use of HBr as the precursor for initiating catalytic oxidation, which is feasible since HBr could be readily in-situ oxidized by $H_2O_2$ to form the catalyst $Br_2$. The key feature of this process is thus the use of $H_2O_2/Br_2$ or $H_2O_2/HBr$ as the viable catalytic oxidation system for converting diols 4-6 into their corresponding products 1-3.

(A)

Step One: Diol Oxidation

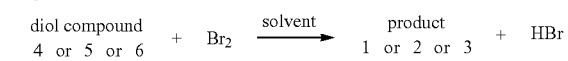

Step Two: $Br_2$ Recovery

(B)

"One-Pot" Process

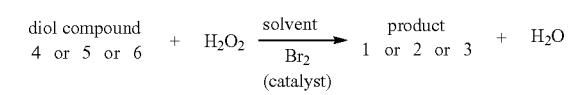

In the above-illustrated reaction scheme A or B, the overall net by-product is water. Among these literature-known disclosures in the related technical field, the present invention offers by far the simplest and most competitive process for preparing the target products, yielding exceptional economic benefits as well as environmental friendliness.

DETAILED EXECUTION

The following examples served to illustrate the invention in more details.

Example 1

Oxidation of Diol 4 into Hydroxyketone Product 1

Process A:

Step one: to a solution of 1662 grams of diol 4 in 20 L of $CH_2Cl_2$ at room temperature was slowly added 1598 grams of Br$_2$ (1 eq), the reaction mixture was stirred while maintaining the reaction system at room temperature, and acidic HBr gas released was absorbed by water. The reaction progress was monitored by TLC until the completion was detected. Water of equal volume was thus added, and organic layer was separated. The solvent was then recovered and the concentrated crude product was subjected to distillation under reduced pressure to yield 1562 grams of hydroxyketone 1 as colorless oil.

Product 1 has the following spectroscopic characterization data:

$^1$H-NMR (CDCl$_3$, ppm): 8.01 (d, 2H), 7.56 (t, 1H), 7.46 (t, 2H), 4.12 (br, 1H), 1.61 (s, 6H);

$^{13}$C-NMR (CDCl$_3$, ppm): 204.7, 133.8, 132.8, 129.6, 128.3, 76.3, 28.3.

Step two: to a well-stirred solution combining the above-obtained aqueous layer and the trapped acidic HBr solution was slowly added 2 equivalents of H$_2$O$_2$ (30% wt solution in water), Br$_2$ of characteristic dark brown color was instantly formed and quantitatively recovered.

Process B:

H$_2$O$_2$/Br$_2$ catalytic system: to a solution containing 1662 grams of diol 4 and 2 equivalents of H$_2$O$_2$ (30% wt solution in water) in 20 L of CH$_2$Cl$_2$ at room temperature was slowly added water to adjust the volume of aqueous layer to be 1/3 of that of organic layer. While maintaining the reaction system at room temperature, 480 grams of Br$_2$ (0.3 eq) was slowly added to the reaction system with vigorous stifling. The reaction progress was monitored by TLC and when needed, an additional amount of H$_2$O$_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1433 grams of hydroxyketone 1 as colorless oil.

H$_2$O$_2$/HBr catalytic system: to a well-stirred solution containing 1662 grams of diol 4 and 2 equivalents of H$_2$O$_2$ (30% wt solution in water) in 20 L of CH$_2$Cl$_2$ at room temperature was slowly added 243 grams of HBr (0.3 eq, 0.5 M aqueous solution). The reaction progress was monitored by TLC and when needed, an additional amount of H$_2$O$_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1336 grams of hydroxyketone 1 as colorless oil.

Example 2

Oxidation of Diol 5 into Hydroxyketone Product 2

Process A:

Step one: to a solution of 2063 grams of diol 5 in 20 L of CH$_2$Cl$_2$ at room temperature was slowly added 1598 grams of Br$_2$ (1 eq), the reaction mixture was stirred while maintaining the reaction system at room temperature, and acidic HBr gas released was absorbed by water. The reaction progress was monitored by TLC until the completion was detected. Water of equal volume was thus added, and organic layer was separated. The solvent was then recovered and the concentrated crude product was subjected to distillation under reduced pressure to yield 1817 grams of hydroxyketone 2 as white solid.

Product 2 has the following spectroscopic characterization data:

$^1$H-NMR (CDCl$_3$, ppm): 8.01-8.00 (d, 2H), 7.55-7.43 (m, 3H), 3.41 (s, 1H), 2.07-2.04 (m, 2H), 1.82-1.66 (m, 8H);

$^{13}$C-NMR (CDCl$_3$, ppm): 205.5, 135.2, 132.3, 129.5, 128.2, 78.7, 35.3, 25.3, 21.4.

Step two: to a well-stirred solution combining the above-obtained aqueous layer and the trapped acidic HBr solution was slowly added 2 equivalents of H$_2$O$_2$ (30% wt solution in water), Br$_2$ of characteristic dark brown color was instantly formed and quantitatively recovered.

Process B:

H$_2$O$_2$/Br$_2$ catalytic system: to a solution containing 2063 grams of diol 5 and 2 equivalents of H$_2$O$_2$ (30% wt solution in water) in 20 L of CH$_2$Cl$_2$ at room temperature was slowly added water to adjust the volume of aqueous layer to be 1/3 of that of organic layer. While maintaining the reaction system at room temperature, 480 grams of Br$_2$ (0.3 eq) was slowly added to the reaction system with vigorous stifling. The reaction progress was monitored by TLC and when needed, an additional amount of H$_2$O$_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1655 grams of hydroxyketone 2 as white solid.

H$_2$O$_2$/HBr catalytic system: to a well-stirred solution containing 2063 grams of diol 5 and 2 equivalents of H$_2$O$_2$ (30% wt solution in water) in 20 L of CH$_2$Cl$_2$ at room temperature was slowly added 243 grams of HBr (0.3 eq, 0.5 M aqueous solution). The reaction progress was monitored by TLC and when needed, an additional amount of H$_2$O$_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1587 grams of hydroxyketone 2 as white solid.

Example 3

Oxidation of Diol 6 into Hydroxyketone Product 3

Process A:

Step one: to a solution of 1962 grams of diol 6 in 20 L of CH$_2$Cl$_2$ at room temperature was slowly added 1598 grams of Br$_2$ (1 eq), the reaction mixture was stirred while maintaining the reaction system at room temperature, and acidic HBr gas released was absorbed by water. The reaction progress was monitored by TLC until the completion was detected. Water of equal volume was thus added, and organic layer was separated. The solvent was then recovered and the concentrated crude product was subjected to distillation under reduced pressure to yield 1372 grams of hydroxyketone 3 as white solid.

Product 3 has the following spectroscopic characterization data:

$^1$H-NMR (CDCl$_3$, ppm): 8.06 (d, 2H, J=7 Hz), 6.94 (d, 2H, J=7 Hz), 4.28 (s, 1H), 3.87 (s, 3H), 1.62 (s, 6H).

Step two: to a well-stirred solution combining the above-obtained aqueous layer and the trapped acidic HBr solution was slowly added 2 equivalents of H$_2$O$_2$ (30% wt solution in water), Br$_2$ of characteristic dark brown color was instantly formed and quantitatively recovered.

Process B:

H$_2$O$_2$/Br$_2$ catalytic system: to a solution containing 1962 grams of diol 6 and 2 equivalents of H$_2$O$_2$ (30% wt solution in water) in 20 L of CH$_2$Cl$_2$ at room temperature was slowly added water to adjust the volume of aqueous layer to be 1/3 of that of organic layer. While maintaining the reaction system at room temperature, 480 grams of Br$_2$ (0.3 eq) was slowly added to the reaction system with vigorous stifling. The reaction progress was monitored by TLC and when needed, an additional amount of $H_2O_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1221 grams of hydroxyketone 3 as white solid.

$H_2O_2$/HBr catalytic system: to a well-stirred solution containing 1962 grams of diol 6 and 2 equivalents of $H_2O_2$ (30% wt solution in water) in 20 L of $CH_2Cl_2$ at room temperature was slowly added 243 grams of HBr (0.3 eq, 0.5 M aqueous solution). The reaction progress was monitored by TLC and when needed, an additional amount of $H_2O_2$ (0.5-2 eq, 30% wt concentration) may be added to aid reaction completion. The reaction system was then diluted with water of equal volume, and the separated organic layer was concentrated and the residue was subjected to distillation under reduced pressure to yield 1109 grams of hydroxyketone 3 as white solid.

It should be emphasized that the above examples serve as illustrative but not limiting embodiments, it is apparent to practitioners in the field that many readily conceivable modifications, changes, and variations of specific reaction conditions can be made without departing from the inventive concept and core reaction features that had already been defined herein. Accordingly, it is intended to embrace all such possible modifications, changes, and variations that fall within the spirit and broad scope defined in the claims associated with this invention.

The invention claimed is:

1. A process for oxidizing a diol compound into a ketone, comprising the following steps of: mixing said diol compound with bromine in an organic solvent; adding water into the mixture when said ketone having been formed, organic layer and aqueous layer being formed; separating organic solution and aqueous solution from said organic layer and said aqueous layer, respectively; purifying said ketone from said organic solution.

2. The process for oxidizing a diol compound into a ketone according to claim 1, wherein said process further comprises: recovering said bromine from said aqueous solution by adding $H_2O_2$.

3. The process for oxidizing a diol compound into a ketone according to claim 1, wherein said diol compound is selected from the group consisting of 2-methyl-1-phenyl-1,2-propanediol, α-(1-hydroxycyclohexyl)-benzene-methanol, and 1-(4-methoxyphenyl)-2-methyl-1,2-propanediol.

4. The process for oxidizing a diol compound into a ketone according to claim 1, wherein said ketone is selected from the group consisting of 2-hydroxy-2-methyl-1-phenyl-1-propanone, (1-hydroxycyclohexyl)phenyl-methanone and 2-hydroxy-1-(4-methoxyphenyl)-2-methyl-1-propanone.

5. The process for oxidizing a diol compound into a ketone according to claim 1, wherein the temperature of reaction is between 10 and 40° C.

6. The process for oxidizing a diol compound into a ketone according to claim 1, wherein said organic solvent consists of halogenated hydrocarbons.

7. A process for oxidizing a diol compound into a ketone, comprising the following steps of: mixing said diol compound with $H_2O_2$ in an organic solvent; adding then bromine or HBr into said solvent; adding more $H_2O_2$ when said ketone being formed, organic layer and aqueous layer being formed; separating organic solution and aqueous solution from said organic layer and said aqueous layer, respectively; and purifying said ketone from said organic solution.

8. The process for oxidizing a diol compound into a ketone according to claim 7, wherein said diol compound is selected from the group consisting of 2-methyl-1-phenyl-1,2-propanediol, α-(1-hydroxycyclohexyl)-benzene-methanol, and 1-(4-methoxyphenyl)-2-methyl-1,2-propanediol.

9. The process for oxidizing a diol compound into a ketone according to claim 7, wherein said ketone is selected from the group consisting of 2-hydroxy-2-methyl-1-phenyl-1-propanone, (1-hydroxycyclohexyl)phenyl-methanone and 2-hydroxy-1-(4-methoxyphenyl)-2-methyl-1-propanone.

10. The process for oxidizing a diol compound into a ketone according to claim 7, wherein the temperature of reaction is between 10 and 40° C.

11. The process for oxidizing a diol compound into a ketone according to claim 7, wherein said organic solvent consists of halogenated hydrocarbons.

* * * * *

UNITED STATES PATENT AND TRADEMARK OFFICE
CERTIFICATE OF CORRECTION

PATENT NO.        : 8,686,191 B2                           Page 1 of 1
APPLICATION NO.   : 13/811903
DATED             : April 1, 2014
INVENTOR(S)       : Ting Chen It is certified that error appears in the above-identified patent and that said Letters Patent is hereby corrected as shown below:

Title page, item [73] Assignee: should read as follows: "SHENZHEN UV –CHEMTECH CO., LTD, SHENZHEN (CN)"

Signed and Sealed this
Third Day of June, 2014

Michelle K. Lee
*Deputy Director of the United States Patent and Trademark Office*